United States Patent
Ransch

(10) Patent No.: US 8,094,014 B2
(45) Date of Patent: Jan. 10, 2012

(54) PACKAGING COMPRISING INTEGRATED SENSOR

(75) Inventor: Pascal Ransch, Meylan (FR)

(73) Assignee: Intuiskin, Crolles (FR)

( * ) Notice: Subject to any disclaimer, the term of this patent is extended or adjusted under 35 U.S.C. 154(b) by 181 days.

(21) Appl. No.: 12/159,681

(22) PCT Filed: Dec. 22, 2006

(86) PCT No.: PCT/FR2006/051416
§ 371 (c)(1),
(2), (4) Date: Jun. 30, 2008

(87) PCT Pub. No.: WO2007/074305
PCT Pub. Date: Jul. 5, 2007

(65) Prior Publication Data
US 2008/0296191 A1    Dec. 4, 2008

(30) Foreign Application Priority Data

Dec. 28, 2005    (FR) ..................................... 05 54120

(51) Int. Cl.
*G08B 13/14*    (2006.01)
(52) U.S. Cl. ..................................... 340/540; 340/572.8
(58) Field of Classification Search .................. 340/540, 340/572.8, 539.1
See application file for complete search history.

(56) References Cited

U.S. PATENT DOCUMENTS

| | | | |
|---|---|---|---|
| 4,736,871 A * | 4/1988 | Luciani et al. .................. | 222/25 |
| 2003/0160021 A1* | 8/2003 | Platt et al. .......................... | 216/2 |
| 2004/0199058 A1* | 10/2004 | Karam et al. .................. | 600/306 |
| 2005/0015005 A1* | 1/2005 | Kockro .......................... | 600/427 |
| 2005/0107125 A1* | 5/2005 | Gilbert ......................... | 455/562.1 |

FOREIGN PATENT DOCUMENTS

| DE | 10144922 | | 4/2003 |
|---|---|---|---|
| EP | 0269317 | | 6/1988 |
| GB | 2 344 101 | * | 5/2000 |
| GB | 2344101 | | 5/2000 |
| WO | 96/02438 | | 2/1996 |
| WO | WO96/02438 | * | 2/1996 |

OTHER PUBLICATIONS

International Search Report PCT/FR2006/051416 dated Apr. 7, 2007.

* cited by examiner

*Primary Examiner* — Shirley Lu
(74) *Attorney, Agent, or Firm* — Heslin Rothenberg Farley & Mesiti P.C.

(57) ABSTRACT

Packaging for receiving a substance having chemical properties which may change between a time when the substance is introduced for the first time into the packaging and a later time when the substance is used, the packaging including
  a main body;
  a closure member;
  a first sensor arranged in the main body and suitable for delivering a signal representing a measurement of a physicochemical property of the substance contained in the packaging;
  a display member for generating visual information representing the measurement;
  a processing unit for conditioning the signal delivered by the first sensor and for displaying the visual information by means of the display member;
  an electric power source for supplying the first sensor, the display member and the processing unit.

23 Claims, 1 Drawing Sheet

PACKAGING COMPRISING INTEGRATED SENSOR

TECHNICAL FIELD OF THE INVENTION

The invention relates to the field of the storage and packaging of substances having particular chemical properties.

The invention relates more particularly to a packaging integrating a measuring member suitable for supplying a user with information relative to various parameters, among which mention can be made in particular of the storage conditions, the time of filling or opening of the packaging, the shelf life, the conditions of the external environment, and also the physicochemical properties of a cutaneous surface. In the context of the present invention, packaging means any device suitable for containing a substance such as, in particular, a container equipped with a closure member, a package, a bottle or a jar.

BRIEF DISCUSSION OF RELATED ART

In general, packagings containing substances whereof the chemical properties may change over time simply comprise an expiry date advising the user to no longer use the substance after the said date.

However, such packagings do not take account of the time when a seal cap is removed from the packaging. They also do not take account of the storage conditions, such as humidity, temperature or external ultraviolet radiation.

The invention seeks to provide a safe, simple and effective solution for preparing a packaging suitable for ensuring a user that the substance that it contains is, for example, fit for use or consumption.

In fact, the invention further seeks to allow the measurement of a physicochemical property of a cutaneous surface of a user, in order to ensure that the substance is compatible with the state of the consumer's skin at the time when he intends to use the substance.

In fact, in general, apparatus for measuring a physicochemical property of a cutaneous surface comprise both a computerised processing unit and a set of sensors positioned in a probe placed in contact with the cutaneous surface.

Such an apparatus has been described in particular by the Applicant in document WO-03/037184. This apparatus is designed to be installed in a dermatological centre or any other dermatological analysis agency. It has the form of a computer equipped with acquisition cards and a probe. It is therefore relatively bulky and hence difficult to transport. In consequence, the number of potential users of this type of apparatus is limited, or persons interested in using it are obliged to go to a place equipped with such an apparatus.

BRIEF SUMMARY OF THE INVENTION

The invention permits the analysis and display of information according to at least one physicochemical parameter of a cutaneous surface. This measurement can be taken regardless of the subject's location, at any time, by means of a miniaturised and self-contained packaging.

The invention further permits the reading of at least one parameter of the external environment in which the measurement of the physicochemical property of the skin or of the substance is taken, or even if no measurement is taken of a physicochemical property.

The invention therefore relates to a packaging for receiving a substance having physicochemical properties which may change between a time when the said substance is introduced for the first time into the packaging and a later time when the said substance is used. This packaging comprises:

a main body;
a closure member;
a first sensor arranged in the main body and suitable for delivering a signal representing a measurement of a physicochemical property of the substance contained in the packaging;
a display member for generating visual information representing the said measurement;
a processing unit for conditioning the signal delivered by the sensor and for displaying the visual information by means of the display member;
an electric power source for supplying the said sensor, the display member and the processing unit.

In other words, the packaging is equipped with at least one sensor for supplying information according to a physicochemical property of the substance, which may be in liquid, viscous or even solid form. The signal or signals delivered by the first sensor are received by a processing unit incorporated in the packaging in the main body or the closure member. These signals are processed in order to permit the display of visual information representing the measurement taken on the substance by the sensor. For this purpose, the processing unit, the first sensor and the display member are supplied with electric power by a self-contained power source integrated in the packaging. These various elements may either be added on to the surface of part of the packaging, or be embedded in the material thereof.

The first sensor may be of the active type, but also in certain cases, passive. It may be prepared from means operating according to electrical or chemical principles, such as a litmus paper or liquid crystals. The first sensor may in particular communicate with the processing unit via a wire link or not, commonly referred to as "wireless". In this case, a Wifi type IT network technology can be used, so that in particular, the first sensor can be placed in the core of the substance to take the measurements of the physicochemical parameter.

Furthermore, the first sensor may either be completely free to move inside the substance, or joined to the inside wall of the main body.

The display means may have liquid crystals or light emitting diodes of the LED or OLED type. They may thus serve to quantitatively display a value level according to the measurement taken.

Such a packaging serves to check the state of development of the chemical properties of the substance at regular intervals, in order to ensure that it is fit for use by a user. This first sensor therefore serves to check the conditions of storage, transfer and use of the substance. In fact, certain products can be maintained at temperatures lower than 10° C. and/or at a low relative humidity to guarantee their shelf life and/or effectiveness.

The substance contained in the packaging may in particular be a cosmetic, pharmaceutical, or even food product. In fact, such substances commonly have a shelf life and chemical properties that may change over time.

In certain specific cases, the packaging may comprise a plurality of sensors selected from the three groups previously described, that is body sensors, atmosphere sensors and content sensors.

In fact, the measurement of the environmental conditions during or between two measurements of the skin provides information considerably improving the interpretation of the results. This is because since the skin is a living organ having a function of regulating exchanges between the human body and its surroundings, it constantly adjusts and modifies its properties according to the environmental conditions. The measurement of these conditions may sometimes even be indispensable for an accurate evaluation of the effectiveness of a cosmetic or medical treatment.

In other cases, it is advantageous to quantify the exposure of the skin to the environmental conditions as a warning of potential pathological risks. For example, controlled environments such as cold rooms, white rooms, blast furnaces, aircraft cockpits, are particularly harmful to the skin, or even the sunlight absorbed during sunbathing or a mountain walk.

Thus, according to a particular embodiment, the conditioning may comprise a second sensor arranged on the closure member. In this way, the second sensor can be handled very easily because it is arranged on a very compact and lightweight part. In certain cases, the closure member may be detached from the main body by means of a screw linkage, the packaging having a thread and the closure member having an internal thread.

In other embodiments, the closure member may be snapped on to the main body and have a hinge type linkage, to prevent the separation of the closure member from the main body.

According to a first embodiment, the second sensor may be a body sensor for delivering a signal representing a physicochemical property of a cutaneous surface.

In this case, the sensor may be in various forms and particularly in the form of a micro-camera. This camera may incorporate a lens and a light source for evaluating the dimensional or colorimetric properties of the skin. The micro-camera may be black/white or colour as required by the measurement to be taken. In fact, such a micro-camera may be suitable for measuring a wrinkle length, its depth, or even the diameter of a pigment spot forming a beauty spot or the quantity of sebum.

In order to improve the taking and subsequent use of the image, an additional element may be associated with the micro-camera and particularly a lighting device, a wide-angle lens, a zoom or a specific wavelength filter.

According to a first alternative, the lighting may be provided by means of a light source inside the packaging.

According to a second alternative, the lighting may also be provided by means of an external light source.

Furthermore, regardless of the alternative used, the light source may comprise light emitting diodes (LED) or organic light emitting diodes (OLED) emitting in the same specific wavelength or several LEDs or OLEDs emitting in different wavelengths. These LEDs or OLEDs may be arranged in circular, triangular or rectangular arrangements around the camera.

The black/white or multicolour lighting modes may be selected by the apparatus automatically or by the user via one or more man-machine interfaces.

In a particular embodiment, a positioning aid may be integrated and provided by at least one oriented LED or OLED pointer. A pattern comprising a simple or complex geometry is projected on the area to be measured. The reflected image of this patent can then be interpreted manually or automatically by the focusing device thereby adjusting the setting of the camera.

In the case in which a zoom is integrated, the system may have means for adjusting same.

The camera is connected to an electronic unit in charge of managing the setting parameters which are the shutter speed, aperture, or even the gain. The light and clarity measurements for adjustment are taken either through the lens of the camera, or by an additional sensor. The image captured by activating a control knob is stored in the onboard storage unit. The format of the captured image is preferably of the compressed type and compatible with the standard formats in force.

The system may integrate image processing algorithms. A man-machine interface, comprising at least one selection knob, enables the user to make a choice from one or more available algorithms according to the measurement that he wishes to take and in particular:
  length of the wrinkles, small wrinkles or microstructures developed;
  area of the wrinkled zones;
  local or average roughness;
  isotropy of the skin;
  local or average colorimetry;
  area of the hyperpigmentation zone;
  measurement of lipids content;
  concentration of hair on the skin.

According to the measurement of the body physicochemical property to be taken, the sensor may also be selected from the group comprising:
  pH sensors;
  cutaneous imprint sensors, suitable for measuring the topography of the cutaneous surface to be analysed;
  skin moisture sensors;
  skin temperature sensors;
  lipids content sensors;
  sensors of elastic deformation of the cutaneous surface to be analysed.

Obviously, for certain applications, the packaging may comprise a plurality of sensors selected from this group and suitable for measuring different physicochemical properties.

The measurement of the skin pH serves to distinguish a high pH, of about 5.5, and a more acid pH, close to 5.

The skin moisture sensor serves to measure very accurately the parameter generally qualified as "Trans Epidermal Water Loss", abbreviated TEWL.

This parameter corresponds to the evaluation of a phenomenon independent of the transpiration, reflected by the evaporation of water from the underlying layers of the epidermis. This measurement serves for example to monitor the hydrolipid film playing the role of a skin barrier function, and to determine the scale of dryness of the skin.

The cutaneous imprint sensor serves to produce a measurement of the various irregularities of the skin surface. This measurement can be taken by various principles such as a capacitive, piezoresistive, piezoelectric, optical or electromagnetic measurement. The determination of the topography of the zone to be analysed serves to measure the uniformity of the skin, the number of wrinkles, their length, area and average depth. The total area of the wrinkles can be determined by calculating the area occupied by the average and deep wrinkles, corresponding respectively to the wrinkles having a depth between 150 and 200 microns, and higher than 200 microns.

It is also possible to determine the intensity of the main lines, in order to determine the length of the deepest wrinkles. The determination of the volume of the main wrinkles serves to measure the evolution of these wrinkles over time.

The measurement of the skin roughness is also an important parameter, because it serves to approach the overall flatness of the skin by characterising it by a mean amplitude value which is the resultant of the various relief features compared to a flat surface. The measurement of this roughness parameter, and its development over time, serves to identify the smoothing of the skin after a particular treatment.

The measurement of the temperature or ambient humidity may serve to correct certain particular measurements, and particularly that of the skin moisture content, that is, the Trans Epidermal Water Loss. It also serves to analyse a diagnosis related to the atmospheric conditions.

The lipids content sensors serve to determine the status of the cutaneous lipids, particularly for dry skins. This measurement serves to distinguish skin dryness phenomena, and excessive sebum production phenomena.

The sensor of elastic deformation of the cutaneous surface to be analysed serves to measure the firmness and elasticity of the skin. This deformation sensor operates on the principle of the application of a vacuum to a zone of skin, during a constant period. Several successive aspirations can be performed in order to measure the depth of penetration of the skin in a part of the packaging. More precisely, this measurement can be taken via optical sensors or based on strain gauges for example.

The analysis of the various measurements obtained serves to distinguish the instantaneous deformations, corresponding to an elasticity mechanism, and the delayed deformations, which can be treated as a viscosity mechanism.

According to a second embodiment, the second sensor may be an atmosphere sensor suitable for delivering a signal representing a measurement of a parameter of the external environment.

In other words, at least one atmosphere sensor serves to supply information according to a parameter of the external environment, such as the temperature, humidity, pressure or fixed or variable frequency electromagnetic wave radiation, such as ultraviolet, infrared, microwave or acoustic waves.

Advantageously, the second sensor may be embedded in the material of the closure member. In fact, this embodiment serves to prevent the second sensor from being damaged by impact with an external element. In certain particular cases, it may however be added on by any method of joining to the outer surface of the closure member.

According to a particular embodiment, the packaging may comprise computation means for measuring the time elapsed since the packaging was filled.

Thus, the packaging may comprise means for detecting the time when the substance is introduced into the packaging, and for storing it and then calculating a duration.

In practice, the packaging may comprise computation means for measuring the time elapsed since the packaging was first opened.

In other words, the packaging may comprise means for detecting the first opening of the packaging particularly by a presence sensor suitable for identifying the absence or presence of the closure member on the main body. Advantageously, the computation means may be integrated in the processing unit in order to generate a signal which can be viewed on the display member.

In fact, the packaging may comprise means for indicating the fact that the interval calculated by the computation means exceeds a predefined threshold. For example, when an expiry date of the substance is reached, the indication means may then display information advising its user that he must no longer use this substance.

In practice, the packaging may comprise means for detecting the positioning of the closure member with regard to the main body corresponding to the open and closed states of the packaging.

Such detection means serve in particular to activate the computation means after the first opening, and also to advise the user when, for example, he has forgotten to reclose the closure member or badly repositioned the closure member on the main body.

Advantageously, the packaging may comprise a buzzer suitable for generating an acoustic signal. In fact, when the closure member is poorly positioned on the main body, an acoustic alarm can then be emitted to serve to avoid any accidental spillage of the substance outside the main body of the packaging.

According to a particular embodiment, the processing unit may comprise a data storage unit. The data delivered by the first or the second sensor for measuring a physicochemical property of the substance or of the surrounding environment may then be stored in order to be used subsequently by means in particular of an auxiliary computerised system.

The packaging may also allow the transfer of the data delivered by the first or the second sensor to a computerised system. In this case, the storage unit may be of the permanent memory type to store information representing the said measurement and to permit its subsequent transfer. The storage unit may thus comprise a capacity to store a substantial number of measurements without the need to transfer the data contained in the storage unit. Once the measurements are taken, the data can therefore be transferred to a computerised system for analysis. This storage capacity may also be used to store information such as identification codes, as well as calibration information, on the state of the first sensor and/or the second sensor and of the packaging. Thus, it is therefore possible to compile a record of the measurements, and also to calculate a relative variation from one measurement to another.

In order to optimise the electric power consumption, the packaging may integrate an energy management system selectively activating and deactivating the various electrical members according to preprogrammed modes, thereby managing the various power modes. This system may integrate charging modes of the electric power source when the packaging is inserted in a specific charger.

The packaging may also comprise an activation member to energise the first sensor, the display member and the processing unit.

Furthermore, the packaging may also comprise "man-machine" interfaces for performing numerous actions according to the version of the packaging used, the type of physicochemical measurement to be taken, and the selection of the algorithm.

The power source may be in the form of a cell or battery which, when a measurement of a physicochemical property of the surrounding environment must be taken, supplies the corresponding sensor, the processing unit, and the display member. When the packaging is not used, the activation member or the electric power management device serves to open the circuit to preserve the electric power stored in the battery and avoid its discharge.

In a first alternative, the electric power source may be a photovoltaic cell. This cell serves to supply electric power to the sensor, the processing unit and the display member. In this case, the power is therefore supplied by the ambient light, and then converted to electrical energy.

In a second alternative, the electric power source may be a microgenerator converting an external energy source to electric power by induction, Hall effect, magnetoresistive, piezoelectric, thermal or mechanical effect.

In a third alternative, the electric power source may also be of a chemical type such as a storage battery, a cell or other battery in particular.

According to a particular embodiment, the sensor may be produced from a micro-electromechanical system (MEMS). An alternative of active or passive sensors may operate according to the principle of MEMS type (micro-electromechanical system) technologies. These sensors are therefore produced according to technologies using semiconductor, insulating or metallic materials, and chemical machining methods employed in the microelectronics field. The use of MEMS type sensors serves to concentrate a large number of sensors on a particularly restricted zone, implanted on the packaging. This serves to obtain results representing a localised, uniform and characteristic zone.

Due to its very small size, the use of MEMS serves advantageously to decrease the power consumption and hence to increase the service life of the electric power source.

According to a particular embodiment, active electric sub-assemblies such as piezo and/or MEMS actuators can perform the measurement sensor control function previously described. This control device may be very useful for repositioning the conditioning on a zone of the skin undergoing treatment observation.

Thus, the MEMS may simultaneously integrate functions of measurement and control of its effectiveness by combining electrical and mechanical devices at very small scale and very low consumption, meeting the major requirements of the packaging.

In order to optimise the contact between the skin and the second body sensor and therefore the efficiency of the measurement, a device for controlling the contact pressure, positioning or orientation, may be integrated in the packaging. The operating principle of this control device may be based on the specific properties of the materials used for the construction of the apparatus and/or the mechanical properties according to the deformations imposed by the specific cutout geometries and/or sandwich assembly arrangements between the various layers of material.

In practice, the packaging may integrate an active or passive calibration device as required. The calibration serves to correct potential drifts of the sensors and to adjust the operating point of the system according to the applications.

BRIEF DESCRIPTION OF THE FIGURES

The manner of implementing the invention and the advantages thereof will appear clearly from the description of the embodiment that follows, provided for information and non-limiting, in conjunction with FIG. 1 schematically showing the packaging according to the invention.

DETAILED DESCRIPTION OF THE INVENTION

Figure 1:
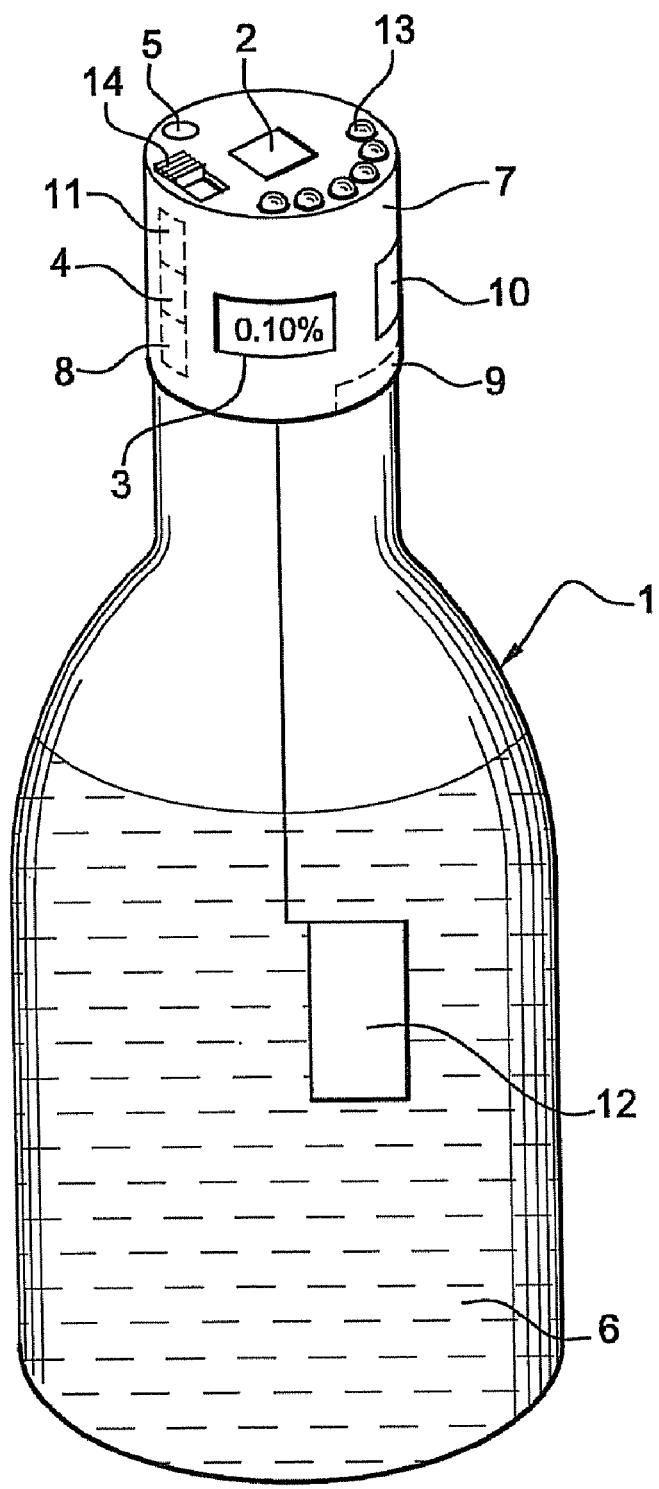

As already stated, the invention relates to a packaging suitable for receiving a substance having chemical properties that are subject to change.

As shown in FIG. 1, the packaging (1) comprises a main body (6) and a closure member (7) joined here by a screw linkage. Such a packaging (1) comprises a first sensor (12) suitable for delivering a signal representing a measurement of a physicochemical property of the substance contained in the main body (6). The first sensor (12) is therefore positioned inside the main body (6).

As shown, the second sensor (2) is arranged on the closure member (7) and serves to take a measurement of a parameter of the external environment, such as the temperature, humidity or intensity of solar radiation. This second sensor (2) may also be a body sensor capable of taking a measurement of a physicochemical property of a cutaneous surface. For this purpose, it is accordingly positioned in contact with the skin of a user.

As shown, the measurements taken by one or the other of the first and second sensors (2, 12) are transferred to the processing unit (4) in order to condition the signal delivered by the sensors and to permit the display of visual information on the display members (3, 13).

The display member (3) may consist of a flexible liquid crystal screen arranged on an outer cylindrical portion of the closure member (7). These display members may also consist of a plurality of light emitting diodes (13) positioned for example on the flat upper surface of the closure member (7).

Such a packaging thus also comprises an electric power source (5) which may in particular be a photovoltaic cell.

At the screw linkage between the closure member (7) and the main body (6), detection means (9) may serve to determine the open or closed status of the packaging (1).

Furthermore, computation means (8) may serve to calculate the time elapsed since, for example, the filling of the packaging with the substance, the first opening, or also upon each opening, in order to advise the user when the period measured by the computation means (8) exceeds a predefined threshold.

These indication means may in particular be in the form of a buzzer (10) arranged on the closure member (7).

In certain particular cases, the data issuing from the first and/or the second sensor (2, 12) are stored in a data storage unit (11). In this way, it is possible to carry out a time analysis of several successive measurements of physicochemical properties of the substance and/or of the external environment.

As shown, the closure member (7) is also equipped with an activation member (14) for energising the sensor or sensors (2, 12), the display member or members (3, 13) and the processing unit (4).

It appears from the above that a packaging according to the invention has many advantages, in particular:
  it serves to ensure with certainty that the substance that it contains is fit for use and has the desired chemical properties;
  it also serves to alert a user when a particular parameter of the surrounding environment is detected or when the latter exceeds a predefined threshold value;
  it enables the user to check that the substance that it contains is compatible with the properties of his cutaneous surface.

The invention claimed is:
1. Packaging for storing a substance having a physicochemical property which may change between a time when said substance is introduced for a first time into the packaging and a later time when said substance is used, said packaging comprising:
  a main body receiving and storing said substance;
  a closure member selectively allowing and preventing access to the substance stored in the main body;
  a first sensor arranged in contact with the substance stored in the main body for delivering a first signal representing a first measurement of the physicochemical property of the substance stored in the main body at said later time;
  a second sensor exposed to an exterior of the packaging for delivering a second signal representing a second measurement of a physicochemical property of a cutaneous surface of a user at said later time;
  a display member for generating visual information representing at least one of said first measurement and said second measurement;
  a processing unit for conditioning at least one of the first signal and the second signal, for displaying the visual information by the display member, and for operating on at least one of the first signal and the second signal for checking that the stored substance is fit for use by the user at the later time, wherein said checking comprises checking that the substance is compatible with the physicochemical properties of the cutaneous surface of the user at the later time;

an electric power source for supplying said first sensor, said second sensor, the display member and the processing unit.

2. Packaging according to claim 1, in combination with the substance, and said substance comprising a cosmetic.

3. Packaging according to claim 1, wherein the second sensor comprises a micro-camera for evaluating dimensional or colorimetric properties of the cutaneous surface.

4. Packaging according to claim 1, further comprising an atmosphere sensor delivering a third signal representing a third measurement of a parameter of the environment external to the main body and the closure member; and wherein the processing unit employs the third signal to at least one of: evaluate effectiveness of a cosmetic substance or medical substance stored in the main body and warn of a potential pathological risk.

5. Packaging according to claim 1, wherein the second sensor is physically associated with the closure member.

6. Packaging according to claim 1, wherein the processing means further comprises computation means for measuring time elapsed since filling of said packaging.

7. Packaging according to claim 1, wherein the processing means further comprises computation means for measuring time elapsed since a first opening of said packaging.

8. Packaging according to claim 6, further comprising means for indicating that a period calculated by the computation means exceeds a predefined threshold.

9. Packaging according to claim 1, further comprising means for detecting a positioning of the closure member with regard to the main body corresponding to open and closed states of said packaging.

10. Packaging according to claim 1, further comprising a buzzer for generating an acoustic signal.

11. Packaging according to claim 1, wherein the processing unit comprises a data storage unit.

12. Packaging according to claim 1, further comprising an activation member for energizing the first sensor, the display member and the processing unit.

13. Packaging according to claim 1, wherein the electric power source is a photovoltaic cell.

14. Packaging according to claim 1, wherein the first sensor is made from micro-electromechanical systems.

15. Packaging according to claim 7, further comprising means for indicating that a period calculated by the computation means exceeds a predefined threshold.

16. Packaging according to claim 1, wherein the first sensor is located in a core of the substance stored in the main body.

17. Packaging according to claim 1, wherein the first sensor is physically unconstrained allowing the first sensor to move inside the substance stored in the main body.

18. Packaging according to claim 3, further comprising an integrated positioning aid for adjusting settings of the micro-camera.

19. Packaging according to claim 3, further comprising an electronic unit connected to the micro-camera for managing setting parameters of the micro-camera.

20. Packaging according to claim 1, wherein the processing unit implements an image processing algorithm to determine at least one of: length of wrinkles, small wrinkles or micro structures; area of wrinkled zones; local or average roughness; isotropy of skin; local or average colorimetry; area of an hyperpigmentation zone; measurement of lipids content; and concentration of hair.

21. Packaging according to claim 1, further comprising an energy management system selectively activating and deactivating electrical components of the packaging to optimize electric power consumption.

22. Packaging according to claim 1, further comprising a device for controlling contact pressure, positioning or orientation to optimize contact between the cutaneous surface and the second sensor.

23. Packaging according to claim 1, wherein said checking that the substance is compatible with the physicochemical properties comprises checking that the substance is fit for use with the cutaneous surface of the user at the later time.

* * * * *